US010646543B2

(12) United States Patent
Gregory et al.

(10) Patent No.: US 10,646,543 B2
(45) Date of Patent: May 12, 2020

(54) METHODS AND COMPOSITIONS FOR TREATING TRINUCLEOTIDE REPEAT DISORDERS

(71) Applicant: Sangamo Therapeutics, Inc., Richmond, CA (US)

(72) Inventors: Philip D. Gregory, Richmond, CA (US); Edward J. Rebar, Richmond, CA (US); H. Steve Zhang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

(21) Appl. No.: 15/916,719

(22) Filed: Mar. 9, 2018

(65) Prior Publication Data
US 2018/0200332 A1    Jul. 19, 2018

Related U.S. Application Data

(60) Division of application No. 14/959,470, filed on Dec. 4, 2015, now Pat. No. 9,943,565, which is a continuation of application No. 12/804,764, filed on Jul. 28, 2010, now Pat. No. 9,234,016.

(60) Provisional application No. 61/271,913, filed on Jul. 28, 2009, provisional application No. 61/273,009, filed on Jul. 29, 2009.

(51) Int. Cl.
A61K 38/17    (2006.01)
C12N 15/90    (2006.01)
C07K 14/47    (2006.01)
A61K 48/00    (2006.01)
A61K 38/00    (2006.01)

(52) U.S. Cl.
CPC .......... *A61K 38/1709* (2013.01); *C07K 14/47* (2013.01); *C12N 15/907* (2013.01); *A61K 38/00* (2013.01); *A61K 48/00* (2013.01); *C07K 2319/00* (2013.01); *C07K 2319/71* (2013.01); *C07K 2319/81* (2013.01)

(58) Field of Classification Search
CPC .... A61K 38/00; A61K 48/00; A61K 38/1709; C12N 15/907; C07K 2319/81; C07K 14/47; C07K 2319/71; C07K 2319/00
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 2002/0115215 A1 | 8/2002 | Wolffe et al. |
| 2002/0160940 A1 | 10/2002 | Case et al. |
| 2003/0082552 A1 | 5/2003 | Wolffe et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0015164 A1 | 1/2008 | Collingwood |
| 2008/0131962 A1 | 6/2008 | Miller |
| 2008/0159996 A1 | 7/2008 | Ando et al. |
| 2009/0068164 A1 | 3/2009 | Segal et al. |
| 2009/0117617 A1 | 5/2009 | Holmes et al. |
| 2009/0305419 A1 | 12/2009 | Miller |
| 2010/0003756 A1 | 1/2010 | Collingwood et al. |

FOREIGN PATENT DOCUMENTS

| | | |
|---|---|---|
| GB | 2338237 A | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |

(Continued)

OTHER PUBLICATIONS

Arnould, et al., "Engineering of Large Number of Highly Specific Homing Endonucleases That Induce Recombination on Novel DNA Targets," *J. Mol. Biol.* 355:443-458 (2006).

(Continued)

*Primary Examiner* — Gregory S Emch
(74) *Attorney, Agent, or Firm* — Pasternak Patent Law

(57) ABSTRACT

Disclosed herein are methods and compositions for treating trinucleotide repeat disorders.

11 Claims, 5 Drawing Sheets

Specification includes a Sequence Listing.

(56) References Cited

FOREIGN PATENT DOCUMENTS

| WO | WO 98/53058 A1 | 11/1998 |
|---|---|---|
| WO | WO 98/53059 A1 | 11/1998 |
| WO | WO 98/53060 A1 | 11/1998 |
| WO | WO 98/54311 A1 | 12/1998 |
| WO | WO 00/023464 A2 | 4/2000 |
| WO | WO 00/27878 A1 | 5/2000 |
| WO | WO 01/60970 A2 | 8/2001 |
| WO | WO 01/88197 A2 | 11/2001 |
| WO | WO 02/008286 A2 | 1/2002 |
| WO | WO 02/016536 A1 | 2/2002 |
| WO | WO 02/044376 A2 | 6/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 2/2007 |
| WO | WO 2007/139898 A2 | 12/2007 |
| WO | WO 2009/042163 A2 | 4/2009 |
| WO | WO 2010/079430 A1 | 7/2010 |
| WO | WO 2010/090744 A1 | 8/2010 |
| WO | WO 2011/011767 A1 | 1/2011 |

OTHER PUBLICATIONS

Beerli, et al., "Engineering Polydactyl Zinc-Finger Transcription Factors," *Nature Biotechnology* 20:135-141 (2002).

Bitinate, et al., "FokI Dimerization Is Required for DNA Cleavage," *PNAS USA* 95:10570-10575 (1998).

Boch, et al., "Breaking the Code of DNA Binding Specificity of TAL-Type III Effectors," *Science* 326:1509-1512 (2009).

Chames, et al., "In Vivo Selection of Engineered Homing Endonucleases Using Double-Strand Break Induced Homologous Recombination," *Nuc Acids Res* 33:e178 (2005).

Choo, et al., "Advances in Zinc Finger Engineering," *Curr. Opin. Struct. Biol.* 10:411-416 (2000).

Davies, et al., "Polyalanine and Polyserine Frameshift Products in Huntington's Disease," *J. of Medical Genetics* 43:893-896 (2006).

Di Prospero, et al., "Therapeutics Development for Triplet Repeat Expansion Diseases," *Nature Reviews Genetics* 6:756-765 (2005).

Graham, et al., "Cleavage At the Caspase-6 Site Is Required for Neuronal Dysfunction and Degeneration Due to Mutant Huntingtin," *Cell* 125:1179-1191 (2006).

Heuer, et al., "Repeat Domain Diversity of AVRBS3-Like Genes in Ralstonia Solanacearum Strains and Association With Host Preferences in the Field," *Appl. and Envir. Micro.* 73:4379-4384 (2007).

Isalan et al., "A Rapid, Generally Applicable Method to Engineer Zinc Fingers Illustrated by Targeting the HIV-1 Promoter," *Nat Biotechnol* 19:656-660 (2001).

Jiang, et al., "Expression, Purification and Characterization of Rat Zinc Finger Protein Mipu in *Escherichia coli*," *Mol. Cell Biochem.* 328(1-2):137-144 (2009).

Kells, et al., "AAV-Mediated Gene Delivery of BDNF or GDNF is Neuroprotective in a Model of Huntington Disease," *Molecular Therapy* 9:682-688 (2004).

Kim, et al., "Chimeric Restriction Endonuclease," *PNAS USA* 91:883-887 (1994).

Kim, et al., "Insertion and Deletion Mutants of FokI Restriction Endonuclease," *J. Biol. Chem.* 269:31978-31981 (1994).

Kim, et al., "Getting a Handhold on DNA: Design of Poly-Zinc Finger Proteins With Femtomolar Dissociation Constents," *PNAS USA* 93:1156-1160 (1996).

Li, et al., "Functional Domains in Fok I Restriction Endonuclease," *PNAS USA* 89:4275-4279 (1992).

Li, et al., "Alteration of the Cleavage Distance of Fok I Restriction Endonuclease by Insertion Mutagenesis," *PNAS USA* 90:2764-2768 (1993).

Mangiarini, et al., "Exon 1 of the HD Gene With an Expanded CAG Repeat Is Sufficient to Cause a Progressive Neurological Phenotype in Transgenic Mice," *Cell* 87:493-506 (1996).

Mittleman, et al., "Zinc-Finger Directed Double-Strand Breaks Within CAG Repeat Tracts Promote Repeat Instabilty in Human Cells," *PNAS USA* 106:9607-9612 (2009).

Moscou, et al., "A Simple Cipher Governs DNA Recognition by TAL Effectors," *Science* 326:1501 (2009).

Nadel, et al., "The Fragile X Syndrome Single Strand D(CGG) Graphic Nucleotide Repeats Readily Fold Back to Form Unimolecular Hairpin Structures," *J Biological Chemistry* 270:28970-28977 (1995).

Orr, et al., "Trinucleotide Rpeat Disorders,"*Annu rev Neurosci.* 30:575-621 (2007).

Pabo, et al., "Design and Selection of Novel CYS2-HIS2 Zinc Finger Proteins," *Ann. Rev. Biochem.* 70:313-340 (2001).

Perez, et al., "Establishment of HIV-1 Resistance in CD4+ T Cells by Genome Editing Using Zinc-Finger Nucleases," *Nature Biotechnology* 26:808-816 (2008).

Remacle, et al., "New Mode of DNA Binding If Multi-Zinc Finger Transcription Factors: δEF1 Family Members Bind With Two Hands to Two Target Sites," *Embo Journal* 18:5073-5084 (1999).

Segal, et al., "Custom DNA-Binding Proteins Come of Age: Polydactyl Zinc-Finger Proteins," *Curr. Opin. Biotechnol.* 12:632-637 (2001).

Timchenko, et al., "Trinucleotide Repeat Disorders in Humans: Discussions of Mechanisms and Medical Issues," *FASEB J* 10:1589-1597 (1996).

Urnov, et al., "Highly Efficient Endogenous Human Gene Correction Using Designed Zinc-Finger Nucleases," *Nature* 435:646-651 (2005).

Van Bilson, et al., "Identification and Ellel-Specific Silencing of the Mutant Huntington Allele in Huntington's Disease Patient-Derived Fibroblasts," *Hum. Gene Ther.* 19(7):710-719.

Walker, et al., "Huntington's Disease," *Lancet* 369:218-228 (2007).

Wheeler, et al., "Length-Dependent Gametic CAG Repeat Instability in the Huntington's Disease Knock-In Mouse," *Hum. Mol.Genet.* 8:115-122 (1999).

Wikipedia printout for "CAG" http://en.wikipedia.org/wiki/CAG (Retrieved Jul. 5, 2012).

Wikipedia printout for "Huntington Disease," http://en.wikipedia.org/w/index/.php?title=Huntington%27s_disease&oldid=303711268 (2009).

Yan, et al., "Progress and Prospects: Techniques for Site-Directed Mutagenesis in Animal Models," *Gene Therapy* 16:581-588 (2009).

Zuccato, et al., "Progressive Loss of BDNF in a Mouse Model of Huntington's Disease and Rescue by BDNF Delivery," *Pharmaclogical Research* 52:133-139 (2005).

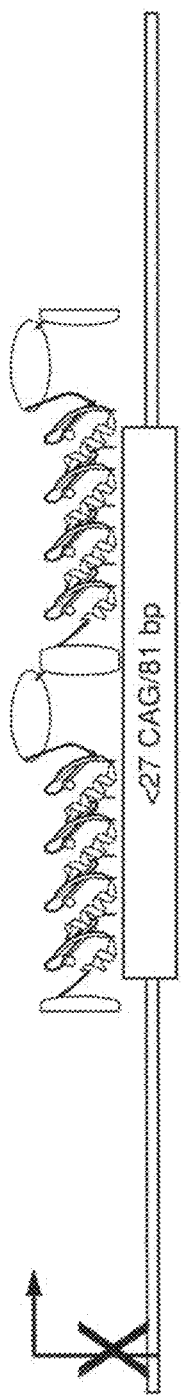
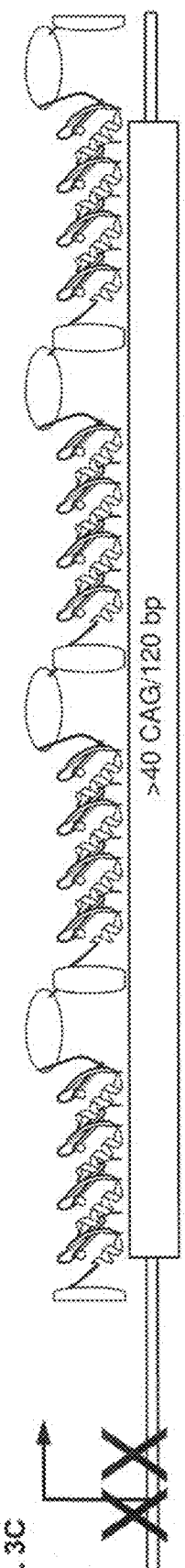
FIG. 3A
FIG. 3B
FIG. 3C

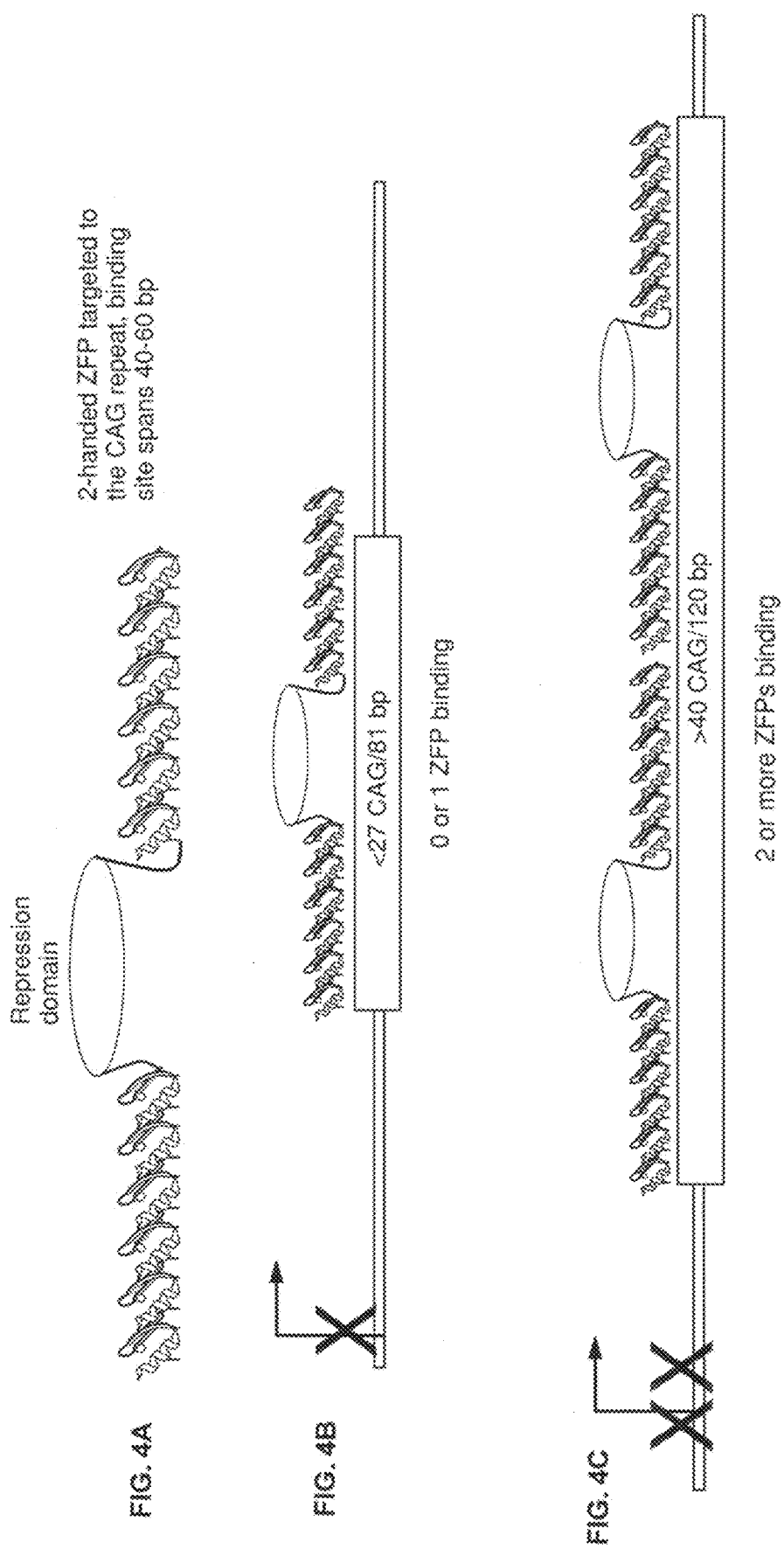

1 = 25920/25921
2 = 25922/25923
3 = GFP
4 = size markers

SEQUENCE LISTING

```
<160> NUMBER OF SEQ ID NOS: 44

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Asp His Leu Ser Arg
1               5

<210> SEQ ID NO 2
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 2

Asp Arg Ser Asn Leu Thr Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ser Ser Asp Leu Arg Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ser Ser Asn Leu Ala Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Arg Ser His Leu Ala Arg
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ser Asp Asp Leu Ser Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Asn Asp Asn Arg Thr Lys
1               5
```

```
<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ser Asp Asp Leu Thr Arg
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Asp Arg Lys Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ala Asp Leu Thr Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Arg Gly Thr Leu Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Asp His Leu Ser Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Arg Ser Asp Val Arg Lys Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Arg Ser Asp Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Arg Ser His Leu Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Asn Asp Asp Arg Lys Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Asp Asn Leu Thr Arg
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Asp Thr Leu Ser Asn
1               5
```

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Asn Ser Asp Arg Thr Lys
1               5

<210> SEQ ID NO 20
<211> LENGTH: 28
<212> TYPE: DNA
<213> ORGANISM: Homo sapiens

<400> SEQUENCE: 20
ggggcgatgc tggggacggg gacattag                                    28

<210> SEQ ID NO 21
<211> LENGTH: 28
<212> TYPE: DNA
<213> ORGANISM: Homo sapiens

<400> SEQUENCE: 21
acgctgcgcc ggcggaggcg gggccgcg                                    28

<210> SEQ ID NO 22
<211> LENGTH: 28
<212> TYPE: DNA
<213> ORGANISM: Homo sapiens

<400> SEQUENCE: 22
aaggcgccgt gggggctgcc gggacggg                                    28

<210> SEQ ID NO 23
<211> LENGTH: 28
<212> TYPE: DNA
<213> ORGANISM: Homo sapiens

<400> SEQUENCE: 23
agtccccgga ggcctcgggc cgactcgc                                    28

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Ser Ala Ala Leu Ser Arg
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 25

Arg Ser Asp Ala Leu Ala Arg
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Arg Ser Asp Asn Leu Ser Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Arg Cys Asn Leu Arg Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Arg Ser Cys Arg Ser Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asp Arg Ser Asn Leu Ser Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Arg Thr His Leu Thr Gln
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Ala His Leu Ser Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Thr Ser Gly His Leu Ser Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ser Ser Asp Leu Ser Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Arg Ser Asp Asn Leu Ala Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ser Gly His Leu Ser Arg
1               5

<210> SEQ ID NO 36
<211> LENGTH: 28
<212> TYPE: DNA
<213> ORGANISM: Homo sapiens

<400> SEQUENCE: 36
gcgctcagca ggtggtgacc ttgtggac                                        28
```

```
<210> SEQ ID NO 37
<211> LENGTH: 28
<212> TYPE: DNA
<213> ORGANISM: Homo sapiens

<400> SEQUENCE: 37
atggtgggag agactgtgag gcggcagc                                           28

<210> SEQ ID NO 38
<211> LENGTH: 28
<212> TYPE: DNA
<213> ORGANISM: Homo sapiens

<400> SEQUENCE: 38
atggcgctca gcaggtggtg accttgtg                                           28

<210> SEQ ID NO 39
<211> LENGTH: 28
<212> TYPE: DNA
<213> ORGANISM: Homo sapiens

<400> SEQUENCE: 39
tgggagagac tgtgaggcgg cagctggg                                           28

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Thr Gly Glu Lys Pro
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Gly Gly Gln Arg Pro
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Gly Gln Lys Pro
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 43

Thr Gly Ser Gln Lys Pro
1               5

<210> SEQ ID NO 44
<211> LENGTH: 9
<212> TYPE: PRT
<213> ORGANISM: Unknown
<220> FEATURE:
<223> OTHER INFORMATION: Description of Unknown: 'LAGLIDADG' family
      peptide

<400> SEQUENCE: 44

Leu Ala Gly Leu Ile Asp Ala Asp Gly
1               5
```

METHODS AND COMPOSITIONS FOR TREATING TRINUCLEOTIDE REPEAT DISORDERS

CROSS-REFERENCE TO RELATED APPLICATIONS

The present application is a divisional of U.S. patent application Ser. No. 14/959,470, filed Dec. 4, 2015, which is a continuation of U.S. patent application Ser. No. 12/804,764, filed Jul. 28, 2010, now U.S. Pat. No. 9,234,016, which claims the benefit of U.S. Provisional Application Nos. 61/271,913, filed Jul. 28, 2009 and 61/273,009, filed Jul. 29, 2009, the disclosures of which are hereby incorporated by reference in their entireties.

STATEMENT OF RIGHTS TO INVENTIONS MADE UNDER FEDERALLY SPONSORED RESEARCH

Not applicable.

TECHNICAL FIELD

The present disclosure is in the fields of gene expression.

BACKGROUND

Trinucleotide repeat expansion disorders were first characterized in the early 1990s (see Di Prospero and Fischbeck, (2005) *Nature Reviews Genetics* vol 6:756-765). These disorders involve the localized expansion of unstable repeats of sets of three nucleotides and can result in loss of function of the gene in which the repeat resides, a gain of toxic function, or both. Trinucleotide repeats can be located in any part of the gene, including non-coding and coding gene regions. Repeats located within the coding regions typically involve either a repeated glutamine encoding triplet (CAG) or an alanine encoding triplet (CGA). Expanded repeat regions within non-coding sequences can lead to aberrant expression of the gene while expanded repeats within coding regions (also known as codon reiteration disorders) may cause mis-folding and protein aggregation. The exact cause of the pathophysiology associated with the aberrant proteins is often not known. Typically, in the wild-type genes that are subject to trinucleotide expansion, these regions contain a variable number of repeat sequences in the normal population, but in the afflicted populations, the number of repeats can increase from, in some cases a simple doubling in the number of repeats, to a log order increase in the number of repeats. For example, in the FMR1 gene, which is subject to CGG expansion in Fragile X patients, the wild-type population displays from 2-50 repeats, while those patients afflicted with Fragile X syndrome can have 200-2000 CGG repeats (Nadel et al., (1995) *Journal Biological Chemistry* 270 (48):28970-28977).

To date, 20 different disorders have been linked to expanded trinucleotide repeats (see Di Prospero and Fischbeck ibid). The phenomenon was first described in spinal and bulbar muscular atrophy (SBMA) wherein a CAG repeat is expanded in a coding region of the androgen receptor. The repeat in the wild-type gene normally comprises 13 to 30 CAGs while SBMA patients can have as many as 40 or more. Other disorders characterized by expanded trinucleotide repeats include Freidreich ataxia (repeats are in the non-coding region of the Fratazin gene), Fragile X Syndromes A and E (repeats are in the non-coding regions of the FMR1 and FMR2 gene, respectively), and Huntington Disease, where repeats are inserted within the N terminal coding region of the large cytosolic protein Huntingtin (Htt). Each polyglutamine expansion disorder displays characteristic pathology, with neuronal loss evident in specific regions of the brain. Polyglutamine expansions in the P/Q Ca2+ channel, in the TATA box binding protein, and in atrophin-1 give rise to spinocerebellar ataxia (SCA)-6, SCA-17, and dentatorubralpallidoluysian atrophy (DRPLA) respectively. Apart from their polyglutamine repeats, the proteins involved in these disorders are unrelated, although they are all widely expressed in both the central nervous system and peripheral tissues.

Huntington's Disease (HD), also known as Huntington's Chorea, is a progressive disorder of motor, cognitive and psychiatric disturbances. The mean age of onset for this disease is age 35-44 years, although in about 10% of cases, onset occurs prior to age 21, and the average lifespan post-diagnosis of the disease is 15-18 years. Prevalence is about 3 to 7 among 100,000 people of western European descent. Normal Htt alleles contain 15-20 CAG repeats, while alleles containing 35 or more repeats can be considered potentially HD causing alleles and confer risk for developing the disease. Alleles containing 36-39 repeats are considered incompletely penetrant, and those individuals harboring those alleles may or may not develop the disease (or may develop symptoms later in life) while alleles containing 40 repeats or more are considered completely penetrant and no asymptomatic persons containing HD alleles with this many repeats have been reported. Those individuals with juvenile onset HD (<21 years of age) are often found to have 60 or more CAG repeats. In addition to an increase in CAG repeats, it has also been shown that HD can involve +1 and +2 frameshifts within the repeat sequences such that the region will encode a poly-serine polypeptide (encoded by AGC repeats in the case of a +1 frameshift) track rather than poly-glutamine (Davies and Rubinsztein (2006) *Journal of Medical Genetics* 43:893-896).

Huntington's Disease is a genetic disease where the HD allele is usually inherited from one parent as a dominant trait. Any child born of a HD patient has a 50% chance of developing the disease if the other parent was not afflicted with the disorder. In some cases, a parent may have an intermediate HD allele and be asymptomatic while, due to repeat expansion, the child manifests the disease. In addition, the HD allele can also display a phenomenon known as anticipation wherein increasing severity or decreasing age of onset is observed over several generations due to the unstable nature of the repeat region during spermatogenesis.

In HD, trinucleotide expansion leads to neuronal loss in the medium spiny gamma-aminobutyric acid (GABA) projection neurons in the striatum, with neuronal loss also occurring in the neocortex. Medium spiny neurons that contain enkephalin and that project to the external globus pallidum are more involved than neurons that contain substance P and project to the internal globus pallidum. Other brain areas greatly affected in people with Huntington's disease include the substantia nigra, cortical layers 3, 5, and 6, the CA1 region of the hippocampus, the angular gyms in the parietal lobe, Purkinje cells of the cerebellum, lateral tuberal nuclei of the hypothalamus, and the centromedial-parafascicular complex of the thalamus (Walker (2007) *Lancet* 369:218-228). The role of the normal Htt protein is poorly understood, but may be involved in neurogenesis, apoptotic cell death, and vesicle trafficking. In addition, there is evidence that wild-type Htt stimulates the production of brain-derived neurotrophic factor (BDNF), a prosurvival factor for the striatal neurons. It has been shown that progression of HD correlates with a decrease in BDNF expression in mouse models of HD (Zuccato et al., (2005) *Pharmacological Research* 52(2):133-139), and that delivery of either BDNF or glial cell line-derived neurotrophic factor (GDNF) via adeno-associated viral (AAV) vector-mediated gene delivery may protect straital neurons in murine models of HD (Kells et al., (2004) *Molecular Therapy* 9(5):682-688).

Treatment options for HD are currently very limited. Some potential methodologies designed to prevent the toxicities associated with protein aggregation that occurs through the extended poly-glutamine tract such as overexpression of chaperonins or induction of the heat shock response with the compound geldanamycin have shown a reduction in these toxicities in in vitro models. Other treatments target the role of apoptosis in the clinical manifestations of the disease. For example, slowing of disease symptoms has been shown via blockage of caspase activity in animal models in the offspring of a pairing of mice where one parent contained a HD allele and the other parent had a dominant negative allele for caspase 1. Additionally, cleavage of HD Htt by caspase may play a role in the pathogenicity of the disease. Transgenic mice carrying caspase-6 resistant mutant Htt were found to maintain normal neuronal function and did not develop striatal neurodegeneration as compared to mice carrying a non-caspase resistant mutant Htt allele. (see Graham et al., (2006) *Cell* 125:1179-1191). Molecules which target members of the apoptotic pathway have also been shown to have a slowing affect on symptomology. For example, the compounds zVAD-fmk and minocycline, both of which inhibit caspase activity, have been shown to slow disease manifestation in mice. The drug remacemide has also been used in small HD human trials because the compound was thought to prevent the binding of the mutant Htt to the NDMA receptor to prevent the exertion of toxic affects on the nerve cell. However, no statistically significant improvements were observed in neuron function in these trials. In addition, the Huntington Study Group conducted a randomized, double-blind study using Co-enzyme Q. Although here was a trend towards slower disease progression among patients that were treated with coenzyme Q10, there was no significant change in the rate of decline of total functional capacity. (Di Prospero and Fischbeck, ibid).

Thus, there remains a need for compositions and methods for the treatment of trinucleotide repeat disorders.

SUMMARY

Disclosed herein are methods and compositions for treating trinucleotide repeat disorders. In particular, provided herein are methods and compositions for modulating expression of a gene comprising a trinucleotide repeat so as to treat trinucleotide repeat disorders, for example, modulating expression of a HD Htt allele so as to treat Huntington disease. Also provided are methods and compositions for generating animal models of trinucleotide repeat disorders.

Thus, in one aspect, engineered zinc finger proteins that modulate expression of a HD allele (e.g., Htt) are provided. Engineered zinc finger proteins are non-naturally occurring zinc finger proteins whose recognition helices have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)).

In some embodiments, the recognition helix is non-naturally occurring. In certain embodiments, the zinc finger proteins have the recognition helices shown in Table 1. In other embodiments, the zinc finger proteins bind to the target sequences shown in Table 2.

In one aspect, two-handed ZFP repressors are provided which are capable of preferentially binding to expanded CAG tracts, but have reduced affinity for wild-type length CAG tracts. In some embodiments, multimerizing ZFP-TFs are used that preferentially bind to expanded trinucleotide tracts but have reduced affinity for trinucleotide repeat tracts of a wild-type length, thereby achieving preferential repression of the expanded allele. In some embodiments, these multimerizing ZFP-TFs achieve cooperative DNA binding to the repeat sequence so that the expanded allele is bound more efficiently by a larger number of ZFPs than the wild-type allele, allowing preferential repression of the mutant allele. In some embodiments, multimerizing ZFP TFs are used that form a stable complex of multimers of a given size, and thus are capable of preferentially interacting with a CAG tract of a certain minimum size, wherein that minimum size is greater than the length of a wild-type CAG tract.

In certain embodiments, the ZFPs as described herein (e.g., two-handed, multimerizing, etc.) preferentially modify expression of a mutant Htt allele. In some embodiments, the ZFP binds specifically to mutant Htt alleles wherein the expanded tract encodes poly-glutamine, while in other embodiments, the ZFP binds specifically to a mutant Htt allele wherein the expansion tract encodes poly-serine. Thus, in some embodiments, the ZFP-TF modulates both the wild type and mutant forms of the Htt allele. In certain embodiments, the ZFP modulates only the wild type Htt allele. In other embodiments, the ZFP modulates only the mutant form of Htt.

In other embodiments, repressing ZFP-TFs are provided which preferentially bind to known SNPs associated with the expanded HD Htt alleles. In this way, the ZFP-TFs are specific for mutant Htt alleles which contain the SNP, allowing for specific repression of the mutant Htt allele. In another aspect, ZFP-TFs that specifically activate the wild-type Htt allele by interacting with SNPs associated with wild-type alleles are provided. In this way, only the wild-type Htt allele is activated.

In another aspect, engineered zinc finger proteins that modulate expression of one or more neurotrophic factors are provided to treat trinucleotide disorders. In some embodiments, the neurotrophic factor(s) modulated is(are) BDNF and/or GDNF. Engineered zinc finger proteins are non-naturally occurring zinc finger proteins whose recognition helices have been altered (e.g., by selection and/or rational design) to bind to a pre-selected target site. Any of the zinc finger proteins described herein may include 1, 2, 3, 4, 5, 6 or more zinc fingers, each zinc finger having a recognition helix that binds to a target subsite in the selected sequence(s) (e.g., gene(s)). In some embodiments, the recognition helices are non-naturally occurring.

In certain embodiments, the zinc finger proteins (ZFPs) as described herein can be placed in operative linkage with a regulatory domain (or functional domain) as part of a fusion protein. By selecting either an activation domain or repression domain for fusion with the ZFP, such fusion proteins can be used either to activate or to repress gene expression. In some embodiments, a fusion protein comprising a ZFP targeted to a mutant Htt as described herein fused to a transcriptional repression domain that can be used to down-regulate mutant Htt expression is provided. In some embodiments, a fusion protein comprising a ZFP targeted to a wild-type Htt allele fused to a transcription activation domain that can upregulate the wild type Htt allele is provided. In certain embodiments, the activity of the regulatory domain is regulated by an exogenous small molecule or ligand such that interaction with the cell's transcription machinery will not take place in the absence of the exogenous ligand. Such external ligands control the degree of interaction of the ZFP-TF with the transcription machinery. The regulatory domain(s) may be operatively linked to any portion(s) of one or more of the ZFPs, including between one or more ZFPs, exterior to one or more ZFPs and any combination thereof.

In some embodiments, the engineered zinc finger proteins as described herein can be placed in operative linkage with nuclease (cleavage) domains as part of a fusion protein. In certain embodiments, such nuclease fusions may be utilized for targeting mutant Htt alleles in stem cells such as induced pluripotent stem cells (iPSC), human embryonic stem cells (hES), mesenchymal stem cells (MSC) or neuronal stem cells wherein the activity of the nuclease fusion will result in an Htt allele containing a wild type number of CAG repeats. In certain embodiments, pharmaceutical compositions comprising the modified stem cells are provided.

In yet another aspect, a polynucleotide encoding any of the zinc finger proteins described herein is provided. Such polynucleotides can be administered to a subject in which it is desirable to treat a trinucleotide repeat disorder.

In still further aspects, the invention provides methods and compositions for the generation of specific model systems for the study of trinucleotide repeat disorders such as Huntington's disease. In certain embodiments, models in which mutant Htt alleles are generated in embryonic stem cells for the generation of cell and animal lines in which trinucleotide expansion tracts of specific lengths (50, 80, 109 and 180 CAG repeats, for example) are inserted into a wild-type Htt allele using zinc finger nuclease (ZFN) driven targeted integration are provided. In certain embodiments, the model systems comprise in vitro cell lines, while in other embodiments, the model systems comprise transgenic animals.

In yet another aspect, a gene delivery vector comprising any of the polynucleotides described herein is provided. In certain embodiments, the vector is an adenovirus vector (e.g., an Ad5/F35 vector), a lentiviral vector (LV) including integration competent or integration-defective lentiviral vectors, or an adenovirus associated viral vector (AAV). Thus, also provided herein are adenovirus (Ad) vectors, LV or adenovirus associate viral vectors (AAV) comprising a sequence encoding at least one zinc finger nuclease (ZFN) and/or a donor sequence for targeted integration into a target gene. In certain embodiments, the Ad vector is a chimeric Ad vector, for example an Ad5/F35 vector. In certain embodiments, the lentiviral vector is an integrase-defective lentiviral vector (IDLV) or an integration competent lentiviral vector. In certain embodiments the vector is pseudo-typed with a VSV-G envelope, or with other envelopes.

In some embodiments, model systems are provided for trinucleotide repeat disorders (e.g., Huntington's disease) wherein the target alleles (e.g., mutant Htt) are tagged with expression markers. In certain embodiments, the mutant alleles (e.g., mutant Htt) are tagged. In some embodiments, the wild type allele (e.g., wild-type Htt) is tagged, and in additional embodiments, both wild type and mutant alleles are tagged with separate expression markers. In certain embodiments, the model systems comprise in vitro cell lines, while in other embodiments, the model systems comprise transgenic animals.

Additionally, pharmaceutical compositions containing the nucleic acids and/or ZFPs (or fusion proteins comprising the ZFPs) are also provided. For example, certain compositions include a nucleic acid comprising a sequence that encodes one of the ZFPs described herein operably linked to a regulatory sequence, combined with a pharmaceutically acceptable carrier or diluent, wherein the regulatory sequence allows for expression of the nucleic acid in a cell. In certain embodiments, the ZFPs encoded are specific for a HD Htt allele. In some embodiments, pharmaceutical compositions comprise ZFPs that modulate a HD Htt allele and ZFPs that modulate a neurotrophic factor. Protein based compositions include one of more ZFPs as disclosed herein and a pharmaceutically acceptable carrier or diluent.

In yet another aspect also provided is an isolated cell comprising any of the proteins, polynucleotides and/or compositions as described herein.

In another aspect, provided herein are methods for treating and/or preventing trinucleotide repeat disorders using the compositions disclosed herein. In certain embodiments, the methods involve treatment of Huntington's disease. In some embodiments, the methods involve compositions where the polynucleotides and/or proteins may be delivered using a viral vector, a non-viral vector (e.g., plasmid) and/or combinations thereof. In some embodiments, the methods involve compositions comprising stem cell populations comprising a ZFP or altered with the ZFNs of the invention.

These and other aspects will be readily apparent to the skilled artisan in light of disclosure as a whole.

BRIEF DESCRIPTION OF THE DRAWINGS

FIG. 1A shows a wild-type Htt allele. FIG. 1B shows a single ZFP-TF binding to an HD Htt allele, where "KRAB" refers to the KRAB repression domain from the KOX1 gene and "ZFP" refers to the zinc finger binding protein. "Standard ZFP TF" is a ZFP transcription factor fusion protein in which the zinc finger binding domains are linked to the KRAB repression domain. FIG. 1C depicts a "two handed ZFP TF," which is a ZFP transcription factor in which two clusters of zinc finger domains are separated by a rigid protein sequences. The functional domain is depicted exterior to one ZFP in this Figure, but it will be apparent that the functional domain may be between the ZFPs or exterior to the ZFPs. FIG. 1D depicts a "multimerizing ZFP TF," which is a ZFP TF that is capable of multimerizing through a multimerization domain (depicted as speckled boxes). Also depicted in FIGS. 1C and 1D as a box with black diamonds is a functional domain (e.g., activation, repression, cleavage domain).

FIGS. 3A through 3C are schematics depicting exemplary multimerizing ZFP-TFs. FIG. 3A shows a single ZFP fused to a functional domain (repression domain) as well as dimerization domains for multimerization. FIG. 3B shows binding of a multimer of two ZFPs as shown in the top line. FIG. 3C shows a multimer of four ZFPs as shown in the top line. It will be apparent that any number of multimers can be used and that the functional domain may be positioned anywhere on one or more of the individual ZFPs.

FIGS. 4A through 4C are schematics depicting exemplary two-handed ZFP-TFs. FIG. 4A shows a two-handed ZFP, including a functional domain positioned between the two ZFPs. As shown in FIG. 1D, the functional domain may be exterior to one of the ZFPs. FIG. 4B depicts binding of the two-handed ZFP to a target site. One or both of the ZFPs will bind to their target sites. FIG. 4C depicts binding of multiple two-handed ZFPs.

DETAILED DESCRIPTION

Figure 1:
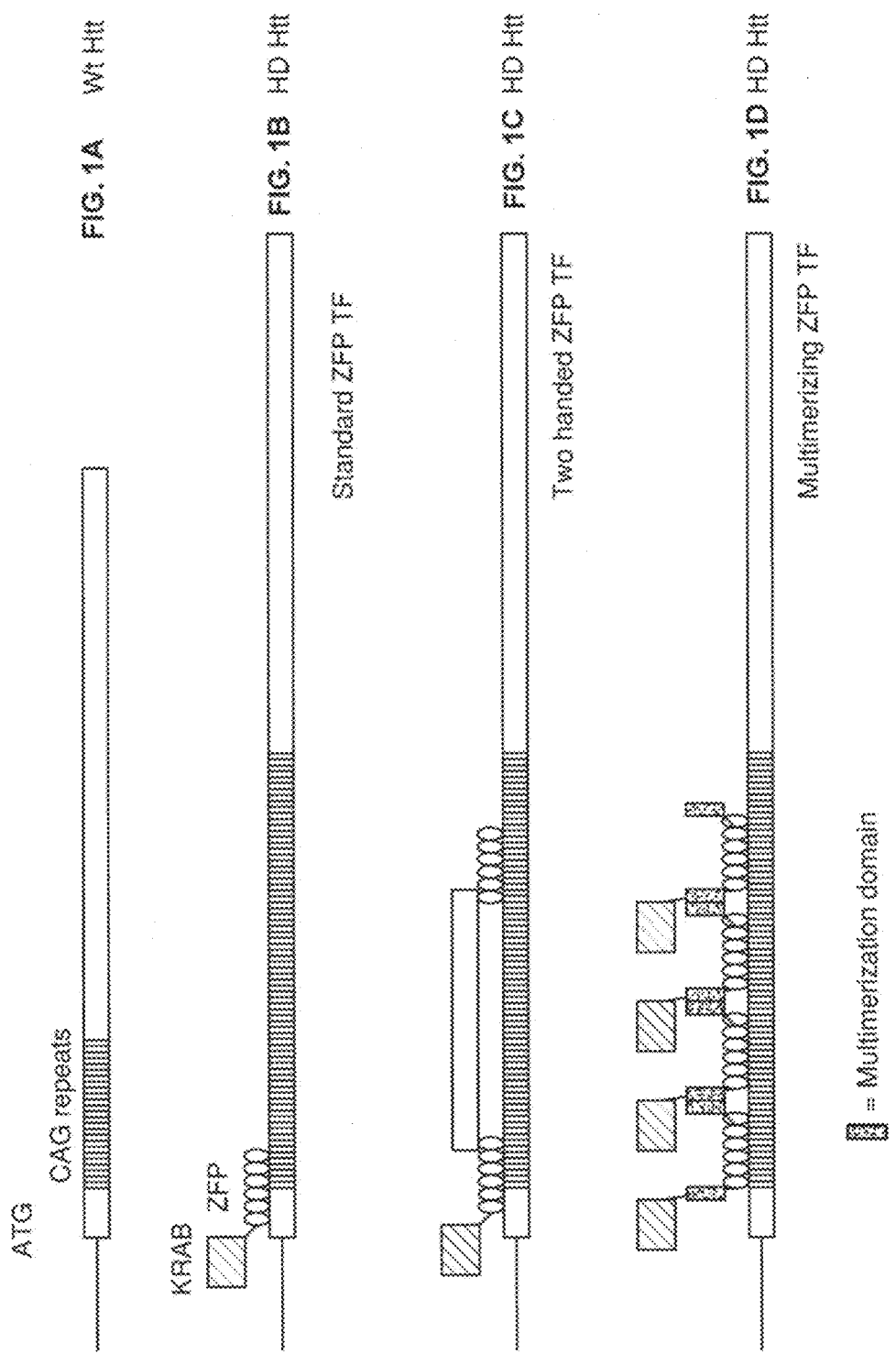
FIGS. 1A through 1D are schematics depicting a Huntingtin (Htt) allele and various ZFP-TFs binding to the allele.

Disclosed herein are compositions and methods for treating trinucleotide repeat disorders such as Huntington's disease, SBMA, Freidreich ataxia, and Fragile X Syndromes A and E and the like. In particular, Htt-modulating transcription factors comprising zinc finger proteins (ZFP TFs) and methods utilizing such proteins are provided for use in treating Huntington's disease. For example, ZFP-TFs which repress expression of a mutant Htt allele or activate expression of a wild-type Htt allele are provided. In addition, zinc finger nucleases (ZFNs) that modify the genomic structure of the genes associated with these disorders are provided. For example, ZFNs that are able to specifically alter portions of a mutant form of Htt are provided. These include compositions and methods using engineered zinc finger proteins, i.e., non-naturally occurring proteins which bind to a predetermined nucleic acid target sequence.

Thus, the methods and compositions described herein provide methods for treatment of trinucleotide repeat disorders, and these methods and compositions can comprise zinc finger transcription factors capable of modulating target genes as well as engineered zinc finger nucleases.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence, for example via engineering (altering one or more amino acids) of the recognition helix region of a naturally occurring zinc finger protein. Therefore, engineered zinc finger proteins are proteins that are non-naturally occurring. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also International Patent Publication Nos. WO 98/53058; WO 98/53059; WO 98/53060; WO 02/016536; and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; and 6,200,759 and International Patent Publication Nos. WO 95/19431; WO 96/06166; WO 98/53057; WO 98/54311; WO 00/27878; WO 01/60970; WO 01/88197; and WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474; 2007/0218528; and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist. Exemplary target sites for various NT-3 targeted ZFPs are shown in Tables 2 and 3.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "multimerization domain" is a domain incorporated at the amino, carboxy or amino and carboxy terminal regions of a ZFP TF. These domains allow for multimerization of multiple ZFP TF units such that larger tracts of trinucleotide repeat domains become bound by multimerized ZFP TFs while wild-type tracts are not. Examples of multimerization domains include leucine zippers. Multimerization domains may also be regulated by small molecules wherein the multimerization domain assumes a proper conformation to allow for interaction with another multimerization domain only in the presence of a small molecule or external ligand. In this way, exogenous ligands can be used to regulate the activity of these domains.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to upregulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al., (1989) *Nature* 340:245-246; U.S. Pat. No. 5,585,245 and International Patent Publication No. PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

DNA-Binding Domains

Described herein are compositions comprising a DNA-binding domain that specifically bind to a target site in any gene comprising a trinucleotide repeat, including, but not limited to, Htt. Also provided are compositions comprising a DNA-binding domain that specifically bind to a target site in a GDNF or BDNF gene. Any DNA-binding domain can be used in the compositions and methods disclosed herein.

In certain embodiments, the DNA binding domain comprises a zinc finger protein. Preferably, the zinc finger protein is non-naturally occurring in that it is engineered to bind to a target site of choice. See, for example, Beerli et al., (2002) *Nature Biotechnol.* 20:135-141; Pabo et al., (2001) *Ann. Rev. Biochem.* 70:313-340; Isalan et al., (2001) *Nature Biotechnol.* 19:656-660; Segal et al., (2001) *Curr. Opin. Biotechnol.* 12:632-637; Choo et al., (2000) *Curr. Opin. Struct. Biol.* 10:411-416; U.S. Pat. Nos. 6,453,242; 6,534,261; 6,599,692; 6,503,717; 6,689,558; 7,030,215; 6,794, 136; 7,067,317; 7,262,054; 7,070,934; 7,361,635; 7,253,273; and U.S. Patent Publication Nos. 2005/0064474; 2007/0218528; and 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. In addition, enhancement of binding specificity for zinc finger binding domains has been described, for example, in co-owned International Patent Publication No. WO 02/077227.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; and 6,200,759 and International Patent Publication Nos. WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536; and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Alternatively, the DNA-binding domain may be derived from a nuclease. For example, the recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al., (1997) *Nucleic Acids Res.* 25:3379-3388; Dujon et al., (1989) *Gene* 82:115-118; Perler et al., (1994) *Nucleic Acids Res.* 22, 1125-1127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 31:2952-2962; Ashworth et al., (2006) *Nature* 441:656-659; Paques et al., (2007) *Current Gene Therapy* 7:49-66; U.S. Patent Publication No. 2007/0117128.

In certain embodiments, the DNA binding domain is an engineered zinc finger protein that binds (in a sequence-specific manner) to a target site in a Htt gene and modulates expression of Htt. The ZFPs can bind selectively to either a mutant Htt allele or a wild-type Htt sequence. Htt target sites typically include at least one zinc finger but can include a plurality of zinc fingers (e.g., 2, 3, 4, 5, 6 or more fingers). Usually, the ZFPs include at least three fingers. Certain of the ZFPs include four, five or six fingers. The ZFPs that include three fingers typically recognize a target site that includes 9 or 10 nucleotides; ZFPs that include four fingers typically recognize a target site that includes 12 to 14 nucleotides; while ZFPs having six fingers can recognize target sites that include 18 to 21 nucleotides. The ZFPs can also be fusion proteins that include one or more regulatory domains, which domains can be transcriptional activation or repression domains.

"Two handed" zinc finger proteins are those proteins in which two clusters of zinc finger DNA binding domains are separated by intervening amino acids so that the two zinc finger domains bind to two discontinuous target sites. An example of a two handed type of zinc finger binding protein is SIP1, where a cluster of four zinc fingers is located at the amino terminus of the protein and a cluster of three fingers is located at the carboxy terminus (see Remade et al., (1999) *EMBO Journal* 18 (18):5073-5084). Each cluster of zinc fingers in these proteins is able to bind to a unique target sequence and the spacing between the two target sequences can comprise many nucleotides. Two-handed ZFPs may include a functional domain, for example fused to one or both of the ZFPs. Thus, it will be apparent that the functional domain may be attached to the exterior of one or both ZFPs (see, FIG. 1C) or may be positioned between the ZFPs (attached to both ZFPs) (see, FIG. 4).

Specific examples of Htt-targeted ZFPs are disclosed in Table 1. The first column in this table is an internal reference name (number) for a ZFP and corresponds to the same name in column 1 of Table 2. "F" refers to the finger and the number following "F" refers which zinc finger (e.g., "F1" refers to finger 1).

TABLE 1

Htt-targeted zinc finger proteins

| SBS # | Design | | | | | |
|---|---|---|---|---|---|---|
| | F1 | F2 | F3 | F4 | F5 | F6 |
| 18832 | RSDHLSR (SEQ ID NO: 1) | DRSNLTR (SEQ ID NO: 2) | RSDHLSR (SEQ ID NO: 1) | QSSDLRR (SEQ ID NO: 3) | QSSNLAR (SEQ ID NO: 4) | DRSHLAR (SEQ ID NO: 5) |
| 18856 | RSDDLSR (SEQ ID NO: 6) | RNDNRTK (SEQ ID NO: 7) | RSDDLTR (SEQ ID NO: 8) | RSDDRKT (SEQ ID NO: 9) | RSADLTR (SEQ ID NO: 10) | QSSDLRR (SEQ ID NO: 3) |

TABLE 1-continued

Htt-targeted zinc finger proteins

| SBS # | F1 | F2 | F3 | F4 | F5 | F6 |
|---|---|---|---|---|---|---|
| 18859 | ERGTLAR (SEQ ID NO: 11) | QSSDLRR (SEQ ID NO: 3) | RSDHLSQ (SEQ ID NO: 12) | RSDVRKN (SEQ ID NO: 13) | DRSDLSR (SEQ ID NO: 14) | DRSH LAR (SEQ ID NO: 5) |
| 18868 | DRSHLTR (SEQ ID NO: 15) | RNDDRKK (SEQ ID NO: 16) | DRSDLSR (SEQ ID NO: 14) | RSDNLTR (SEQ ID NO: 17) | RSDTLSN (SEQ ID NO: 18) | TNSD RTK (SEQ ID NO: 19) |
| 25920 | RSAALSR (SEQ ID NO: 24) | RSDALAR (SEQ ID NO: 25) | RSDNLSE (SEQ ID NO: 26) | KRCNLRC (SEQ ID NO: 27) | QSSDLRR (SEQ ID NO: 3) | N/A |
| 25921 | WRSCRSA (SEQ ID NO: 28) | DRSNLSR (SEQ ID NO: 29) | QRTHLTQ (SEQ ID NO: 30) | RSAHLSR (SEQ ID NO: 31) | TSGHLSR (SEQ ID NO: 32) | N/A |
| 25922 | RSAALSR (SEQ ID NO: 24) | RSDALAR (SEQ ID NO: 25) | RSDNLSE (SEQ ID NO: 26) | KRCNLRC (SEQ ID NO: 27) | QSSDLSR (SEQ ID NO: 33) | DRSH LAR (SEQ ID NO: **5) |
| 25923 | RSDDLSR (SEQ ID NO: 6) | RNDNRTK (SEQ ID NO: 7) | WRSCRSA (SEQ ID NO: 28) | RSDNLAR (SEQ ID NO: 34) | QSGHLSR (SEQ ID NO: 35) | N/A |

The sequence and location for the target sites of these proteins are disclosed in Table 2. Table 2 shows target sequences for the indicated zinc finger proteins. Nucleotides in the target site that are contacted by the ZFP recognition helices are indicated in uppercase letters; non-contacted nucleotides indicated in lowercase.

TABLE 2

Target sites on human Htt

| SBS # | Target Site |
|---|---|
| 18832 | GgGGCGATGCTGGGGACGGGgacattag (SEQ ID NO: 20) |
| 18856 | AcGCTGCGCCGGCGGAGGCGggccgcg (SEQ ID NO: 21) |
| 18859 | AaGGCGCCGTGGGGGCTGCCgggacggg (SEQ ID NO: 22) |
| 18868 | AgTCCCCGGAGGCCTCGGGCcgactcgc (SEQ ID NO: 23) |
| 25920 | gcGCTCAGCAGGTGGTGaccttgtggac (SEQ ID NO: 36) |
| 25921 | atGGTGGGAGAGACTGTgaggcggcagc (SEQ ID NO: 37) |
| 25922 | atGGCGCTCAGCAGGTGGTGaccttgtg (SEQ ID NO: 38) |
| 25923 | tgGGAGAGAcTGTGAGGCGgcagctggg (SEQ ID NO: 39) |

Fusion Proteins

Fusion proteins comprising DNA-binding proteins (e.g., ZFPs) as described herein and a heterologous regulatory (functional) domain (or functional fragment thereof) are also provided. Common domains include, e.g., transcription factor domains (activators, repressors, co-activators, co-repressors), silencers, oncogenes (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g. kinases, acetylases and deacetylases); and DNA modifying enzymes (e.g., methyltransferases, topoisomerases, helicases, ligases, kinases, phosphatases, polymerases, endonucleases) and their associated factors and modifiers. U.S. Patent Publication Nos. 2005/0064474; 2006/0188987 and 2007/0218528 for details regarding fusions of DNA-binding domains and nuclease cleavage domains, incorporated by reference in their entireties herein Suitable domains for achieving activation include the HSV VP16 activation domain (see, e.g., Hagmann et al., *J. Virol.* 71, 5952-5962 (1997)) nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); Liu et al., *Cancer Gene Ther.* 5:3-28 (1998)), or artificial chimeric functional domains such as VP64 (Beerli et al., (1998) *Proc. Natl. Acad. Sci. USA* 95:14623-33), and degron (Molinari et al., (1999) *EMBO J.* 18, 6439-6447). Additional exemplary activation domains include, Oct 1, Oct-2A, Sp1, AP-2, and CTF1 (Seipel et al., *EMBO J.* 11, 4961-4968 (1992) as well as p300, CBP, PCAF, SRC1 PvALF, AtHD2A and ERF-2. See, for example, Robyr et al., (2000) *Mol. Endocrinol.* 14:329-347; Collingwood et al., (1999) *J. Mol. Endocrinol.* 23:255-275; Leo et al., (2000) *Gene* 245:1-11; Manteuffel-Cymborowska (1999) *Acta Biochim. Pol.* 46:77-89; McKenna et al., (1999) *J. Steroid Biochem. Mol. Biol.* 69:3-12; Malik et al., (2000) *Trends Biochem. Sci.* 25:277-283; and Lemon et al., (1999) *Curr. Opin. Genet. Dev.* 9:499-504. Additional exemplary activation domains include, but are not limited to, OsGAI, HALF-1, C1, AP1, ARF-5, -6, -7, and -8, CPRF1, CPRF4, MYC-RP/GP, and TRAB1. See, for example, Ogawa et al., (2000) *Gene* 245:21-29; Okanami et al., (1996) *Genes Cells* 1:87-99; Goff et al., (1991) *Genes Dev.* 5:298-309; Cho et al., (1999) *Plant Mol. Biol.* 40:419-429; Ulmason et al., (1999) *Proc. Natl. Acad. Sci. USA* 96:5844-5849; Sprenger-Haussels et al., (2000) *Plant J.* 22:1-8; Gong et al., (1999) *Plant Mol. Biol.* 41:33-44; and Hobo et al., (1999) *Proc. Natl. Acad. Sci. USA* 96:15,348-15,353.

It will be clear to those of skill in the art that, in the formation of a fusion protein (or a nucleic acid encoding same) between a DNA-binding domain and a functional domain, either an activation domain or a molecule that interacts with an activation domain is suitable as a functional domain. Essentially any molecule capable of recruiting an activating complex and/or activating activity (such as, for example, histone acetylation) to the target gene is useful as an activating domain of a fusion protein. Insulator domains, localization domains, and chromatin remodeling proteins such as ISWI-containing domains and/or methyl binding domain proteins suitable for use as functional domains in fusion molecules are described, for example, in co-owned U.S. Patent Publication Nos. 2002/0115215 and 2003/0082552 and in co-owned International Patent Publication No. WO 02/44376.

Exemplary repression domains include, but are not limited to, KRAB A/B, KOX, TGF-beta-inducible early gene (TIEG), v-erbA, SID, MBD2, MBD3, members of the DNMT family (e.g., DNMT1, DNMT3A, DNMT3B), Rb, and MeCP2. See, for example, Bird et al., (1999) *Cell* 99:451-454; Tyler et al., (1999) *Cell* 99:443-446; Knoepfler et al., (1999) *Cell* 99:447-450; and Robertson et al., (2000) *Nature Genet.* 25:338-342. Additional exemplary repression domains include, but are not limited to, ROM2 and AtHD2A. See, for example, Chem et al., (1996) *Plant Cell* 8:305-321; and Wu et al., (2000) *Plant J.* 22:19-27.

Fusion molecules are constructed by methods of cloning and biochemical conjugation that are well known to those of skill in the art. Fusion molecules comprise a DNA-binding domain and a functional domain (e.g., a transcriptional activation or repression domain). Fusion molecules also optionally comprise nuclear localization signals (such as, for example, that from the SV40 medium T-antigen) and epitope tags (such as, for example, FLAG and hemagglutinin). Fusion proteins (and nucleic acids encoding them) are designed such that the translational reading frame is preserved among the components of the fusion.

Fusions between a polypeptide component of a functional domain (or a functional fragment thereof) on the one hand, and a non-protein DNA-binding domain (e.g., antibiotic, intercalator, minor groove binder, nucleic acid) on the other, are constructed by methods of biochemical conjugation known to those of skill in the art. See, for example, the Pierce Chemical Company (Rockford, Ill.) Catalogue. Methods and compositions for making fusions between a minor groove binder and a polypeptide have been described. Mapp et al., (2000) *Proc. Natl. Acad. Sci. USA* 97:3930-3935.

In certain embodiments, the target site bound by the zinc finger protein is present in an accessible region of cellular chromatin. Accessible regions can be determined as described, for example, in co-owned International Patent Publication No. WO 01/83732. If the target site is not present in an accessible region of cellular chromatin, one or more accessible regions can be generated as described in co-owned International Patent Publication No. WO 01/83793. In additional embodiments, the DNA-binding domain of a fusion molecule is capable of binding to cellular chromatin regardless of whether its target site is in an accessible region or not. For example, such DNA-binding domains are capable of binding to linker DNA and/or nucleosomal DNA. Examples of this type of "pioneer" DNA binding domain are found in certain steroid receptor and in hepatocyte nuclear factor 3 (HNF3). Cordingley et al., (1987) *Cell* 48:261-270; Pina et al., (1990) *Cell* 60:719-731; and Cirillo et al., (1998) *EMBO J.* 17:244-254.

The fusion molecule may be formulated with a pharmaceutically acceptable carrier, as is known to those of skill in the art. See, for example, Remington's Pharmaceutical Sciences, 17th ed., 1985; and co-owned International Patent Publication No. WO 00/42219.

The functional component/domain of a fusion molecule can be selected from any of a variety of different components capable of influencing transcription of a gene once the fusion molecule binds to a target sequence via its DNA binding domain. Hence, the functional component can include, but is not limited to, various transcription factor domains, such as activators, repressors, co-activators, co-repressors, and silencers.

Additional exemplary functional domains are disclosed, for example, in co-owned U.S. Pat. No. 6,534,261 and U.S. Patent Publication No. 2002/0160940.

Functional domains that are regulated by exogenous small molecules or ligands may also be selected. For example, RheoSwitch® technology may be employed wherein a functional domain only assumes its active conformation in the presence of the external RheoChem™ ligand (see for example U.S. Patent Publication No. 2009/0136465). Thus, the ZFP may be operably linked to the regulatable functional domain wherein the resultant activity of the ZFP-TF is controlled by the external ligand.

Nucleases

In certain embodiments, the fusion protein comprises a DNA-binding binding domain and cleavage (nuclease) domain. As such, gene modification can be achieved using a nuclease, for example an engineered nuclease. Engineered nuclease technology is based on the engineering of naturally occurring DNA-binding proteins. For example, engineering of homing endonucleases with tailored DNA-binding specificities has been described. Chames et al., (2005) *Nucleic Acids Res* 33(20):e178; Arnould et al., (2006) *J Mol. Biol.* 355:443-458. In addition, engineering of ZFPs has also been described. See, e.g., U.S. Pat. Nos. 6,534,261; 6,607,882; 6,824,978; 6,979,539; 6,933,113; 7,163,824; and 7,013,219.

In addition, ZFPs have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al., (1996) *Proc Natl Acad Sci USA* 93(3):1156-1160. More recently, ZFNs have been used for genome modification in a variety of organisms. See, for example, U.S. Patent Publication Nos. 2003/0232410; 2005/0208489; 2005/0026157; 2005/0064474; 2006/0188987; and 2006/0063231 and International Patent Publication No. WO 07/014275.

Thus, the methods and compositions described herein are broadly applicable and may involve any nuclease of interest. Non-limiting examples of nucleases include meganucleases and zinc finger nucleases. The nuclease may comprise heterologous DNA-binding and cleavage domains (e.g., zinc finger nucleases; meganuclease DNA-binding domains with heterologous cleavage domains) or, alternatively, the DNA-binding domain of a naturally-occurring nuclease may be altered to bind to a selected target site (e.g., a meganuclease that has been engineered to bind to site different than the cognate binding site).

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 44) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al., (1997) Nucleic Acids Res. 25:3379-3388; Dujon et al., (1989) Gene 82:115-118; Perler et al., (1994) Nucleic Acids Res. 22, 1125-1127; Jasin (1996) Trends Genet. 12:224-228; Gimble et al., (1996) J. Mol. Biol. 263:163-180; Argast et al., (1998) J. Mol. Biol. 280:345-353 and the New England Biolabs catalogue.

DNA-binding domains from naturally-occurring meganucleases, primarily from the LAGLIDADG (SEQ ID NO: 44) family, have been used to promote site-specific genome modification in plants, yeast, *Drosophila*, mammalian cells and mice, but this approach has been limited to the modification of either homologous genes that conserve the meganuclease recognition sequence (Monet et al., (1999), Biochem. Biophysics. Res. Common. 255:88-93) or to pre-engineered genomes into which a recognition sequence has been introduced (Route et al., (1994), Mol. Cell. Biol. 14:8096-106; Chilton et al., (2003), Plant Physiology. 133:956-65; Puchta et al., (1996), Proc. Natl. Acad. Sci. USA 93:5055-60; Rong et al., (2002), Genes Dev. 16:1568-81; Gouble et al., (2006), J. Gene Med. 8(5):616-622). Accordingly, attempts have been made to engineer meganucleases to exhibit novel binding specificity at medically or biotechnologically relevant sites (Porteus et al., (2005), Nat. Biotechnol. 23:967-73; Sussman et al., (2004), J. Mol. Biol. 342:31-41; Epinat et al., (2003), Nucleic Acids Res. 31:2952-62; Chevalier et al., (2002) Molec. Cell 10:895-905; Epinat et al., (2003) Nucleic Acids Res. 31:2952-2962; Ashworth et al., (2006) Nature 441:656-659; Paques et al., (2007) Current Gene Therapy 7:49-66; U.S. Patent Publication Nos. 2007/0117128; 2006/0206949; 2006/0153826; 2006/0078552; and 2004/0002092). In addition, naturally-occurring or engineered DNA-binding domains from meganucleases have also been operably linked with a cleavage domain from a heterologous nuclease (e.g., FokI).

In other embodiments, the nuclease is a zinc finger nuclease (ZFN). ZFNs comprise a zinc finger protein that has been engineered to bind to a target site in a gene of choice and cleavage domain or a cleavage half-domain.

As described in detail above, zinc finger binding domains can be engineered to bind to a sequence of choice. See, for example, Beerli et al., (2002) *Nature Biotechnol.* 20:135-141; Pabo et al., (2001) *Ann. Rev. Biochem.* 70:313-340; Isalan et al., (2001) *Nature Biotechnol.* 19:656-660; Segal et al., (2001) *Curr. Opin. Biotechnol.* 12:632-637; Choo et al., (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as International Patent Publication Nos. WO 98/37186; WO 98/53057; WO 00/27878; and WO 01/88197 and GB 2,338,237. In addition, enhancement of binding specificity for zinc finger binding domains has been described, for example, in co-owned International Patent Publication No. WO 02/077227.

Selection of target sites; ZFNs and methods for design and construction of fusion proteins (and polynucleotides encoding same) are known to those of skill in the art and described in detail in U.S. Patent Publication Nos. 2005/0064474 and 2006/0188987, incorporated by reference in their entireties herein.

In addition, as disclosed in these and other references, zinc finger domains and/or multi-fingered zinc finger proteins may be linked together using any suitable linker sequences, including for example, linkers of 5 or more amino acids in length (e.g., TGEKP (SEQ ID NO:40), TGGQRP (SEQ ID NO:41), TGQKP (SEQ ID NO:42), and/or TGSQKP (SEQ ID NO:43)). See, e.g., U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. See, also, U.S. Provisional Patent Application No. 61/343,729.

Nucleases such as ZFNs and/or meganucleases also comprise a nuclease (cleavage domain, cleavage half-domain). As noted above, the cleavage domain may be heterologous to the DNA-binding domain, for example a zinc finger DNA-binding domain and a cleavage domain from a nuclease or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al., (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al., (eds.) *Nucleases, Cold Spring Harbor Laboratory Press,* 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150; and 5,487,994; as well as Li et al., (1992) *Proc. Natl. Acad. Sci. USA* 89:4275-4279; Li et al., (1993) *Proc. Natl. Acad. Sci. USA* 90:2764-2768; Kim et al., (1994a) *Proc. Natl. Acad. Sci. USA* 91:883-887; Kim et al., (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al., (1998) *Proc. Natl. Acad. Sci. USA* 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Publication No. WO 07/014275, incorporated herein in its entirety. Additional restriction enzymes also contain separable binding and cleavage domains, and these are contemplated by the present disclosure. See, for example, Roberts et al., (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 2005/0064474; 2006/0188987; and 2008/0131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KIK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Provisional Patent Application No. 61/337,769 filed Feb. 8, 2010).

Engineered cleavage half-domains described herein can be prepared using any suitable method, for example, by site-directed mutagenesis of wild-type cleavage half-domains (Fok I) as described in U.S. Patent Publication Nos. 2005/0064474 and 2008/0131962.

Alternatively, nucleases may be assembled in vivo at the nucleic acid target site using so-called "split-enzyme" technology (see e.g. U.S. Patent Publication No. 2009/0068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

In some embodiments, the DNA binding domain is an engineered domain from a TAL effector similar to those derived from the plant pathogens Xanthomonas (see Boch et al., (2009) *Science* 326:1509-1512 and Moscou and Bogdanove, (2009) *Science* 326:1501) and Ralstonia (see Heuer et al., (2007) *Applied and Environmental Microbiology* 73(13):4379-4384). Also, see International Patent Publication No. WO 2010/079430.

Nucleases (e.g., ZFNs) can be screened for activity prior to use, for example in a yeast-based chromosomal system as described in International Patent Publication No. WO 2009/042163 and U.S. Patent Publication No. 2009/0068164. Nuclease expression constructs can be readily designed using methods known in the art. See, e.g., U.S. Patent Publication Nos. 2003/0232410; 2005/0208489; 2005/0026157; 2005/0064474; 2006/0188987; 2006/0063231; and International Patent Publication No. WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Delivery

The proteins (e.g., ZFPs), polynucleotides encoding same and compositions comprising the proteins and/or polynucleotides described herein may be delivered to a target cell by any suitable means including, for example, by injection of ZFP TF or ZFN mRNA. Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as *Spodoptera fugiperda* (Sf), or fungal cells such as *Saccharomyces, Pichia* and *Schizosaccharomyces*. In certain embodiments, the cell line is a CHO-K1, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering proteins comprising zinc finger proteins as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Zinc finger proteins as described herein may also be delivered using vectors containing sequences encoding one or more of the zinc finger protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more zinc finger protein-encoding sequences. Thus, when one or more ZFPs are introduced into the cell, the ZFPs may be carried on the same vector or on different vectors. When multiple vectors are used, each vector may comprise a sequence encoding one or multiple ZFPs.

Conventional viral and non-viral based gene transfer methods can be used to introduce nucleic acids encoding engineered ZFPs in cells (e.g., mammalian cells) and target tissues. Such methods can also be used to administer nucleic acids encoding ZFPs to cells in vitro. In certain embodiments, nucleic acids encoding ZFPs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, Science 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, International Patent Publication Nos. WO 91/17424 and WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al., (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); and International Patent Publication No. WO 1994/026877).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; International Patent Publication No. WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6 and AAV8, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFP nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic*

Technique (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+(T cells), CD45+(panB cells), GR-1 (granulocytes), and Tad (differentiated antigen presenting cells) (see Inaba et al., *J. Exp. Med.* 176:1693-1702 (1992)).

Stem cells that have been modified may also be used in some embodiments. For example, neuronal stem cells that have been made resistant to apoptosis may be used as therapeutic compositions where the stem cells also contain the ZFP TFs of the invention. Resistance to apoptosis may come about, for example, by knocking out BAX and/or BAK using BAX- or BAK-specific ZFNs (see, U.S. Pat. No. 8,597,912) in the stem cells, or those that are disrupted in a caspase, again using caspase-6 specific ZFNs for example. These cells can be transfected with the ZFP TFs that are known to regulate mutant or wild-type Htt.

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al., (1996) *Proc. Natl. Acad. Sci. USA* 93:11382-11388; Dull et al., (1998) *J. Virol.* 72:8463-8471; Zuffery et al., (1998) *J. Virol.* 72:9873-9880; Follenzi et al., (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NS0, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces.* Progeny, variants and derivatives of these cell lines can also be used.

Applications

The disclosed compositions and methods can be used for any application in which it is desired to modulate genes associated with trinucleotide repeat disorders and/or to remove tracts of trinucleotide repeats in genes associated with these disorders. In particular, these methods and compositions can be used where modulation of Htt allele is desired, including but not limited to, therapeutic and research applications.

Diseases and conditions which HD Htt repressing ZFP TFs can be used as therapeutic agents include, but are not limited to, Huntington's disease. Additionally, methods and compositions comprising ZFNs specific for mutant alleles of Htt can be used as a therapeutic for the treatment of Huntington's disease.

ZFP-TFs that repress a HD Htt allele may also be used in conjunction with ZFP-TFs that activate neutrotrophic factors including, but not limited to, GDNF and BDNF. These ZFPs (or polynucleotides encoding these ZFPs) may be administered concurrently (e.g., in the same pharmaceutical compositions) or may be administered sequentially in any order.

Methods and compositions for the treatment of Huntington's disease also include stem cell compositions wherein a mutant copy of the Htt allele within the stem cells has been modified to a wild-type Htt allele using a Htt-specific ZFN.

The methods and compositions of the invention are also useful for the design and implementation of in vitro and in vivo models, for example, animal models of trinucleotide repeate disorders, which allows for the study of these disorders.

EXAMPLES

Example 1: Design and Construction of Htt-Targeted Zinc Finger Protein Transcription Factors (ZFP-TFs)

Zinc finger proteins targeted to Htt were engineered essentially as described in U.S. Pat. No. 6,534,261. Table 1 shows the recognition helices DNA binding domain of exemplary Htt-targeted ZFPs.

Two handed ZFP-TFs are also constructed using two separate clusters of zinc finger binding domain essentially as described above except that the final vector comprises two arrays of ZFPs flanking the gene sequence of a two handed ZFP-TF such as SIP1. See, FIG. 1C and FIG. 4.

Multimerizing ZFP TFs are also constructed as described above except that the vector contains sequences encoding 1 or more multimerazation domains that enable multimerization of the expressed protein along a tract of trinucleotide repeats that is operably linked to the sequences encoding the ZFP TF. See, FIG. 1D and FIG. 3.

ZFP TF were constructed as fusion proteins comprising a nuclear localization sequence, the engineered zinc finger DNA-binding domain (see Table 1) targeted to the Htt allele, and a KRAB repression domain from the human KOX1 protein. See, FIG. 1A. The designed DNA-binding domains contain six finger modules, recognizing 18-bp sequences (see Table 2). Nucleotides in the target site that are contacted by the ZFP recognition helices are indicated in uppercase letters; non-contacted nucleotides indicated in lowercase.

ELISA based assay are used to confirm ZFP binding to the target sequences. Briefly, an expression cassette coding for Hemagglutinin epitope (HA)-tagged full-length ZFP under the control of T7 promoter is created by PCR amplification from each of the assembled ZFP, using primers which introduce the T7 promoter and the coding sequence for the HA-tag. This PCR fragment is used to generate the HA-tagged ZFP protein in vitro by using the TNT Quick Coupled Transcription and Translation System (Promega, Wis., USA); the HA-tagged protein is then mixed with the biotinylated DNA oligos containing the intended target site within the Htt gene, as well as the competitor (human genomic) DNA, to permit only specific ZFP-DNA recognition to be reported.

The ZFP-DNA complexes are then labeled with a peroxidase-conjugated anti-HA antibody, followed by capturing on streptavidin coated 96-well plate. The specific ZFP-DNA complexes are then quantified by assaying the captured peroxidase activity using QuantaBlu (Pierce, Rockford, Ill.) as a substrate. ZFP TF specific for the mouse or human Htt promoter and exon 1 are designed and tested for binding to target sequences.

Example 2: Repression of HD Htt in Human and Mouse Cells

To test the activity of the Htt repressing ZFP TFs, the ZFP TFs were transfected into human cells and expression of Htt was monitored using PCR.

Initially, standard ZFP TFs shown in Table 1 were tested. Human 293 cells (Graham et al., (1977). *J Gen Virol* 36:59-74) were cultured in DMEM supplemented with 10% FBS. Ninety-six-well plates were seeded at a density of 1e4 cells per well and transfected the following day with 0.1 ug of plasmid DNA encoding ZFP-TFs 18832, 18856, 18859 and 18868 using the Fugene6 reagent following the manufacturer's instructions. Transfected cells were incubated for 3 days and then processed using the Cells-to-CT™ Kit (Applied Biosystems) for gene expression analysis. The levels of endogenous human Huntingtin (Htt) relative to internal control beta-actin (ACTB) were analyzed by real-time PCR on a TaqMan® 7300 using Hs00918176_m1 and 4352935E primers and probes (Applied Biosystems), respectively.

Figure 2:
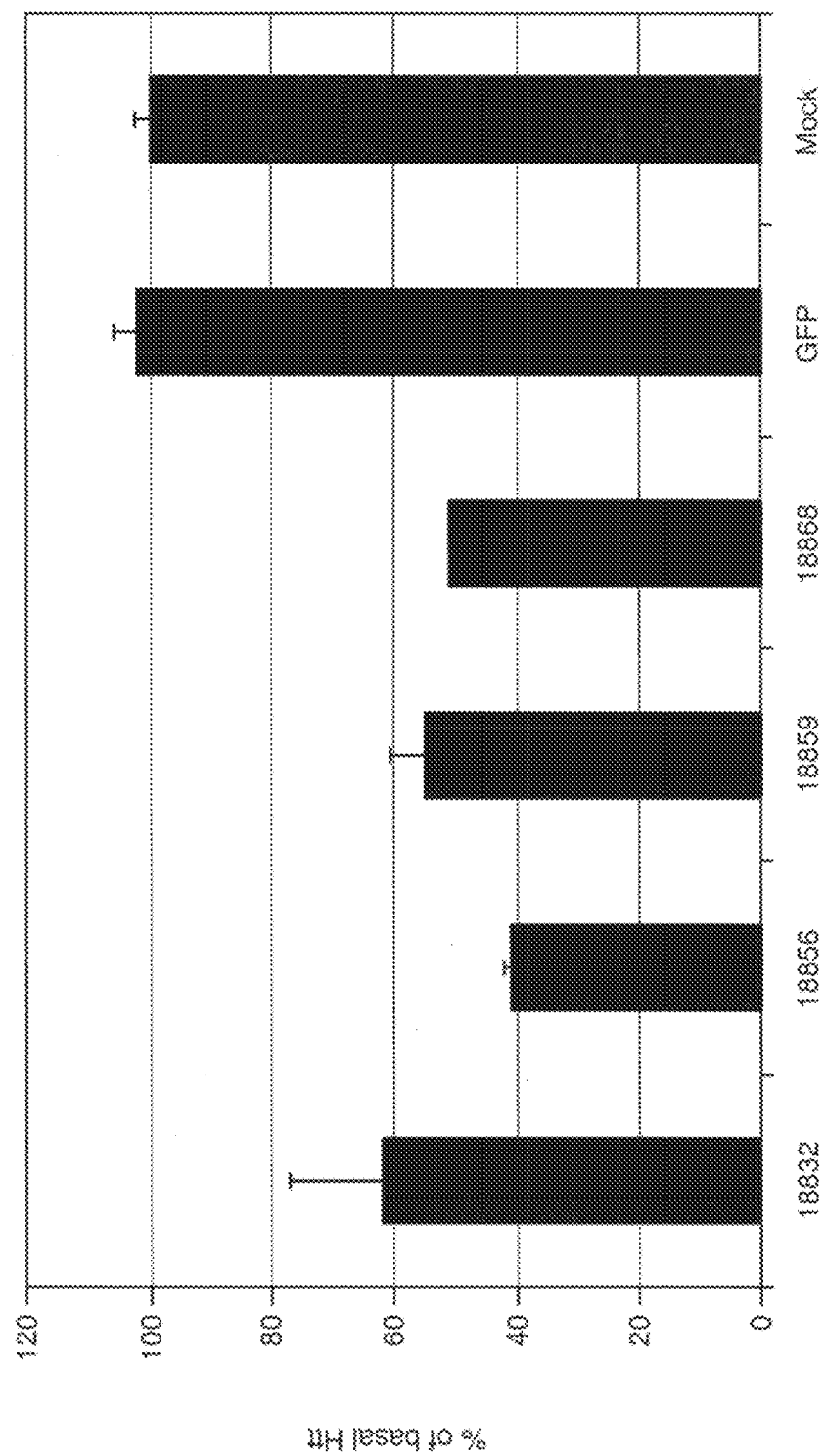
FIG. 2 depicts the repression of Htt by the standard ZFP TFs in human 293T cells (listed in Table 1). GFP indicates a ZFP TF specific for GFP and Mock indicates expression in cells that have been mock transfected.

As shown in FIG. 2, ZFP-TFs repressed Htt expression as compared to GFP and mock controls. Results are expressed in percentage of basal Htt relative to ACTB endogenous levels.

To test the activity of the two handed and multimerizing ZFP TFs, the same protocol is followed using two-handed and multimerizing ZFPs.

To test the ZFP TFs with specificity for the human HD Htt allele, the Htt-specific ZFP TFs are transiently transfected into SH-SY5Y neuroblastoma cells (Biedler J L, et al., (1978) Cancer Res. 38:3751-3757). Briefly, the assembled ZFP-TF constructs are cloned into pcDNA vectors (InVitrogen) and transfected using the Fugene6 kit (Roche Applied Science) according to manufacturer's protocol. Htt expression levels are measured using real-time RT-PCR (TaqMan®, Applied Biosystems) using the Hs00918176_m1 primer/probe set purchased from Applied Biosystems. Western blot analyses are done to confirm a reduction in Htt protein level.

To test the Htt-specific ZFP TFs designed to interact with the mouse alleles, the constructs encoding the mouse ZFP TFs are cloned into pcDNA vectors and transiently transfected into Neuro-2A cells (Klebe & Ruddle (1969) *J Cell Biol.* 43:69A) or an equivalent murine neuronal cell line expressing mouse Htt, using the Lipofectamine 2000 kit (Invitrogen) according to manufacturer's protocols. Htt expression levels are measured using real-time RT-PCR. Western blot analyses are done to confirm a reduction in Htt protein level.

In addition, the human Htt-specific ZFP TFs are tested in primary neuronal cells derived from R6.2 transgenic mice carrying a truncated human Htt allele with CAG expansion (Mangiarini et al., (1996) *Cell* 87:493-506). Mouse Htt-specific ZFP TFs, as well as ZFPs that target the CAG repeats (2-handed ZFPs and ZFPs with multimerization domains) are tested in immortalized striatal cells derived from Htt knock-in mice (Wheeler et al., (1999) Hum Mol Genet. January; 8(1):115-22).

Example 3: Repression of Htt Expression In Vivo

To test the Htt-specific ZFP TFs in vivo, AAV2 vectors encoding the ZFPs are produced. These AAV2 based constructs are then delivered to the brain of mice. For human Htt-specific ZFP TFs, AAV vectors are delivered to R6.2 mice or BAC HD mice (C57Bl/6 or FVB/N strains) to assess the repression of the human transgene. For mouse Htt-specific ZFPs, AAV vectors are delivered to wild-type mice (C57Bl/6 or FVB/N) to assess the repression of the endogenous mouse Htt expression. For ZFPs that preferentially targeting the CAG-expanded allele, AAV vectors are delivered to R6.2 mice or human Htt knock-in mice to examine the selective repression of wt vs. expanded Htt allele. Following sacrifice, brain tissues are analyzed for Htt expression by Taqman real-time RT-PCR.

Example 4: Co-Transfection of a Neurotrophic Factor and a HD Htt Allele-Specific ZFP TF The Htt-specific ZFP TFs identified above are co-transfected with ZFP TFs-specific for a brain neurotrophic factor. The ZFP TF specific for brain neurotrophic factors used are specific for either GDNF or BDNF.

Example 5: Design and Construction of Htt-Targeted Zinc Finger Nucleases (ZFNs)

ZFNs targeting human Htt and mouse Htt are designed to target the sequences flanking the CAG repeats as well as sequences in the first and last coding exon. ZFNs were designed and incorporated into plasmids or adenoviral vectors essentially as described in Urnov et al., (2005) *Nature* 435(7042):646-651, Perez et al., (2008) *Nature Biotechnology* 26(7):808-816, and U.S. Patent Publication No. 2008/0131962.

As described above, the assembled ZFNs are tested for binding to their respective target sequences by ELISA.

Example 6: Cleavage Activity of Htt-Specific ZFNs

To test cleavage activity, plasmids encoding the pairs of human Htt-specific ZFNs described above are transfected into K562 cells. K562 cells were obtained from the American Type Culture Collection and grown as recommended in F-12 medium (Invitrogen) supplemented with 10% qualified fetal calf serum (FCS, Cyclone). Cells were disassociated from plastic ware using TrypLE Select™ protease (Invitrogen). For transfection, one million K562 cells were mixed with 2 μg of the zinc-finger nuclease plasmid and 100 μL Amaxa Solution T. Cells were transfected in an Amaxa Nucleofector II™ using program U-23 and recovered into 1.4 mL warm F-12 medium+10% FCS.

Genomic DNA is harvested and a portion of the Htt locus encompassing the intented cleavage site is PCR amplified. PCR using the Accuprime HiFi polymerase from InVitrogen is performed as follows: after an initial 3 minute denaturation at 94° C., 30 cycles of PCR are performed with a 30 second denaturation step at 94° C. followed by a 30 second annealing step at 58° C. followed by a 30 second extension step at 68° C. After the completion of 30 cycles, the reaction is incubated at 68° C. for 7 minutes, then at 10° C. indefinitely.

The genomic DNA from the K562 Htt-specific ZFN treated cells is examined by the Surveyor™ nuclease (Transgenomic) as described, for example, in U.S. Patent Publication Nos. 2008/0015164; 2008/0131962; and 20080159996.

Plasmids encoding the pairs of mouse Htt-specific ZFNs are tested in similar fashion in Neuro-2a cells.

Example 7: Targeted Integration of Varying Lengths of Trinucleotide Repeats

The Htt-specific ZFNs with the greatest cleaving activity for sequences flanking the CAG repeat as described above are used in a targeted integration strategy to introduce varying lengths of CAG repeat into a wild-type copy of Htt. Donors are constructed that contain 50, 80, 109 and 180 repeat CAG units. These donors are then transfected into K562 cells with plasmids encoding the Htt-specific ZFNs as described above. Verification of donor integration is achieved by genomic DNA isolation, PCT amplification (as described above) followed by sequencing of the region of interest.

ZFNs identified in the K562 cells which result in targeted integration of the donor alleles into the Htt allele are used to insert the variable length donor nucleic acids into human embryonic stem cells (hESC). Successful donor integration is verified by genomic DNA isolation, PCR and sequencing as described above.

Example 8: Expression Tagging of Wild-Type and HD Murine Htt Alleles

ZFNs with the greatest cleaving activity for the first or last coding exon are used to tag the wild-type and mutant Htt allele with different reporter proteins. Donor DNAs for each reporter (A and B) are designed based on the cleavage site of the lead ZFN pair(s) to allow targeted integration of the reporter gene to produce an in-frame fusion to Htt. Donor DNAs are co-transfected with the lead ZFN pair(s) into Neuro-2A cells for selecting the donor DNA construct that gives the highest frequency of integration.

Figure 5:
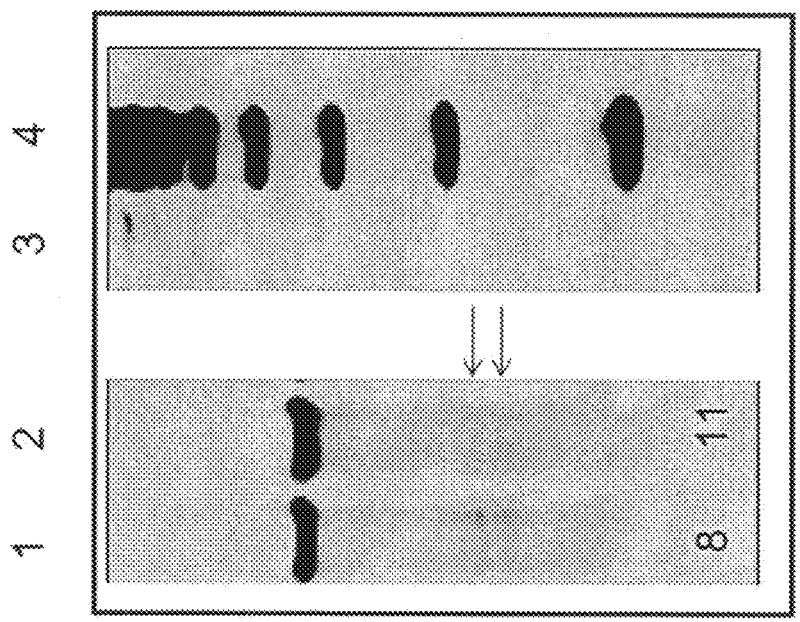
FIG. 5 depicts a gel showing the results of a Cel-I mismatch assay (Surveyor, Transgenomics) following treatment of K562 cells with either the Htt specific ZFN pair 25920/25921 or 25922/25923. The percent NHEJ activity is shown at the bottom of each lane. "GFP" indicates cells that have been transfected with a GFP encoding plasmid. Data shown is from DNA that had been extracted 14 days post transfection with the ZFN containing plasmids.

ZFN pairs 25920/25921 and 25922/25923 were prepared as described above and tested for cleavage activity using the Cel I mismatch as described for Example 6. These ZFN pairs target the 3' end of the Htt gene sequence, and thus may be used to target either a wild-type or a mutant Htt allele. The results are displayed in FIG. 5. As can be seen from the figure, these two pairs are capable of cleaving the Htt gene and can thus be utilized for the introduction of a reporter.

The selected donor DNA construct for reporter A along with corresponding ZFNs are delivered to mouse embryonic stems cells derived from model mice that contain an expanded Htt allele (e.g. Human Htt knock-in mice). Clones are derived and screened for the target integration of the reporter A. Heterozygous events are desired and the targeted allele are identified by PCR. Clones containing a single reporter-tagged Htt allele and unmodified ZFN target sequence on the other allele are selected; the donor construct for reporter B and corresponding ZFNs are trasfected to tag the second allele with the reporter B.

The resulting mouse embryonic stem cell clone contains the wild-type Htt allele and mutant allele tagged with two different markers that allow tracking of expression from each allele; these cells are used to generate mouse models of trinucleotide repeat disorders using standard protocols.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of repressing Htt expression in a cell, the method comprising providing a non-naturally occurring transcription factor that represses expression of an Htt gene, wherein the transcription factor comprises a repression domain and a zinc finger DNA-binding domain that binds to a target site of at least 9 nucleotides of the target sites as set forth in any of SEQ ID NO:20-23 and 36-39, wherein the zinc finger DNA-binding domain comprises a zinc finger protein that comprises 5 or 6 zinc finger recognition regions, ordered F1 to F5 or F1 to F6 from N-terminus to C-terminus, wherein the zinc finger protein comprises the recognition regions in the order shown in a single row of Table 1.

2. The method of claim 1, wherein the Htt gene is wild-type.

3. The method of claim 2, wherein the DNA-binding domain binds to a SNP associated with a wild-type allele.

4. The method of claim 1, wherein the Htt gene comprises one or more expanded trinucleotide repeats.

5. The method of claim 4, wherein the expanded trinucleotide repeat encodes poly-glutamine.

6. The method of claim 4, wherein the expanded trinucleotide repeat encodes poly-serine.

7. The method of claim 4, wherein the DNA-binding domain binds to a SNP associated with the expanded trinucleotide repeat.

8. The method of claim 1, comprising providing a multimer comprising at least two zinc finger proteins that preferentially binds to expanded trinucleotide tracts as compared to wild-type trinucleotide repeat tracts.

9. The method of claim 1, wherein the non-naturally occurring transcription factor is provided as a polynucleotide encoding the protein.

10. The method of claim 9, wherein the polynucleotide is a viral or non-viral vector.

11. A method of treating Huntington's disease in a subject in need thereof, the method comprising repressing Htt expression in a cell of the subject according to the method of claim 1.

* * * * *